United States Patent
Chapsky et al.

(10) Patent No.: US 6,989,235 B2
(45) Date of Patent: Jan. 24, 2006

(54) SINGLE MOLECULE DETECTION OF BIO-AGENTS USING THE F1-ATPASE BIOMOLECULAR MOTOR

(75) Inventors: Lars Chapsky, Tempe, AZ (US); Wayne D. Frasch, Phoenix, AZ (US); Chia Fu Chou, Chandler, AZ (US); Frederic Zenhausern, Fountain Hills, AZ (US); Herbert Goronkin, Tempe, AZ (US)

(73) Assignee: Motorola, Inc., Schaumburg, IL (US)

( * ) Notice: Subject to any disclaimer, the term of this patent is extended or adjusted under 35 U.S.C. 154(b) by 409 days.

(21) Appl. No.: 10/365,378

(22) Filed: Feb. 11, 2003

(65) Prior Publication Data

US 2003/0215844 A1    Nov. 20, 2003

Related U.S. Application Data

(60) Provisional application No. 60/357,163, filed on Feb. 13, 2002.

(51) Int. Cl.
*C12Q 1/68*    (2006.01)
*C12P 19/34*    (2006.01)

(52) U.S. Cl. .......................... 435/6; 435/91.1; 435/91.2
(58) Field of Classification Search ................ 422/80, 422/82.01, 82.05; 435/6; 536/24.3, 24.33
See application file for complete search history.

(56) References Cited

U.S. PATENT DOCUMENTS 6,232,066 B1 * 5/2001 Felder et al. .................. 435/6
6,613,516 B1 * 9/2003 Christians et al. ............. 435/6

OTHER PUBLICATIONS

Noji et al., "Direct observation of the rotation of F1-ATPase," Nature, Mar. 1997, vol. 386, pp. 299-302.*
Frasch et al., "Molecular Motors: ATP Synthase," on line publication, 2001, http://photoscience.la.asu.edu/bionano/research4.htm.*

* cited by examiner

*Primary Examiner*—Kenneth R. Horlick
*Assistant Examiner*—Young J. Kim

(57) ABSTRACT

An exemplary system and method of employing DNA hybridization for the detection of bio-agents is disclosed as comprising inter alia a biomolecular rotary motor (150); a capture probe DNA fragment (140) effectively attached to said biomolecular motor (150); a target DNA fragment (130) suitably adapted for hybridization with said capture probe DNA (140); a signal probe DNA fragment (120) suitably adapted for hybridization with said target DNA (130); and a fluorescent bead (100) attached to said signal probe DNA (120). Disclosed features and specifications may be variously controlled, adapted or otherwise optionally modified to improve certain device fabrication parameters and/or performance metrics.

20 Claims, 2 Drawing Sheets

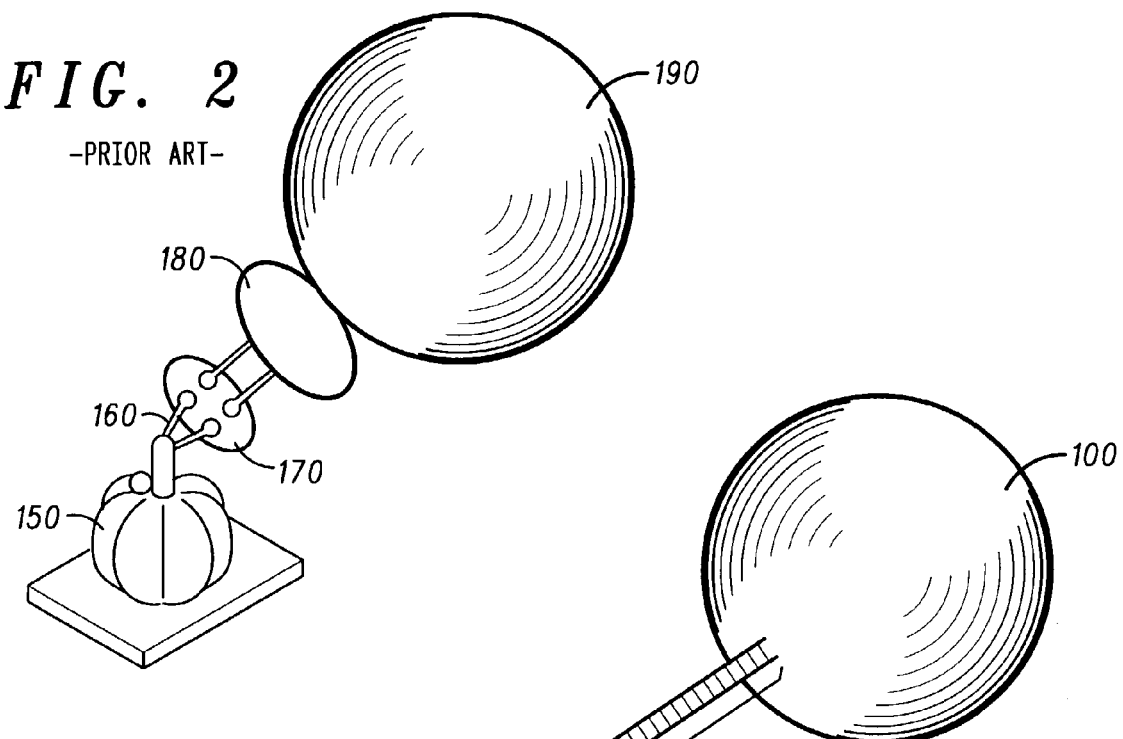
*FIG. 2*
-PRIOR ART-
*FIG. 1*
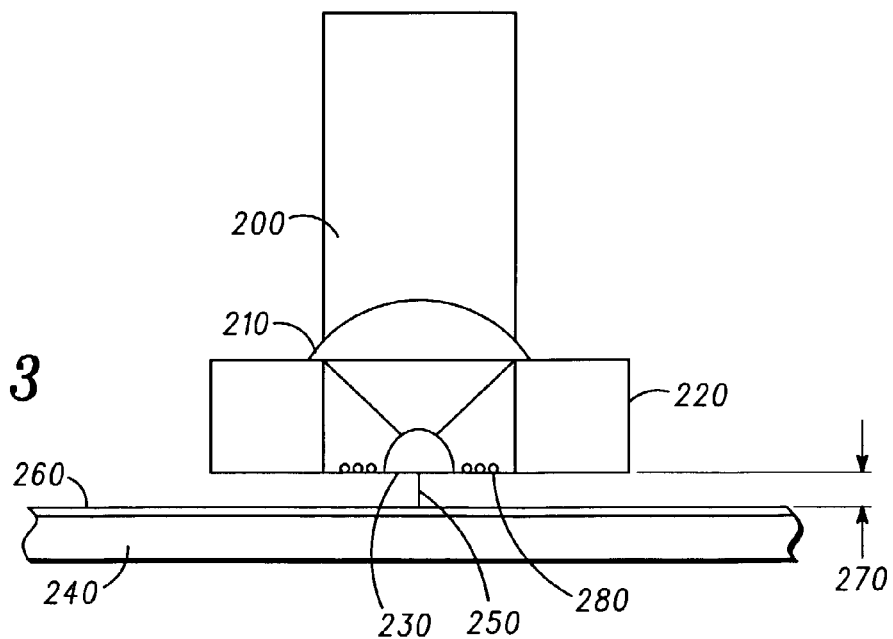
*FIG. 3*

SINGLE MOLECULE DETECTION OF BIO-AGENTS USING THE F1-ATPASE BIOMOLECULAR MOTOR

RELATED APPLICATIONS

This application claims priority to and the benefit of U.S. Provisional Patent Application Ser. No. 60/357,163 filed Feb. 13, 2002.

FIELD OF INVENTION

The present invention generally concerns DNA microarray technology; and more particularly, in one representative and exemplary embodiment, a system and method for employing DNA hybridization techniques for inter alia the detection of bio-agents.

BACKGROUND

With the threat of biological warfare being much more probable in light of recent attacks on the United States, a rapid and sensitive means to detect bio-agents is desirable if treatments for infection are to be administered in time to prevent loss of life. Conventionally, it may take several days to verify the presence of, for example, anthrax and such tests generally only test for the presence of a single agent.

Micro-array technology holds the promise of increased diversity, speed and sensitivity in the identification of several bioactive agents. Devices that deliver pre-synthesized oligonucleotides in small, well-defined spots onto solid substrates using ink-jet delivery may be employed to create DNA arrays that may be used to test for a large number of analytes on a chip the size of a microscope slide; however, there are current limitations to conventional detection sensitivities. Generally, DNA micro-arrays require sample volumes on the order of about 10–50 $\mu L$ and (for most practical platforms) the detection sensitivities only reach about 100 fM or about 0.6E9 molecules. Some magnetoresistive techniques currently in development at the Naval Research Laboratory are anticipated to improve conventional detection limits by at least three orders of magnitude; however, this is still far from the regime of single molecule detection. Accordingly, despite the efforts of the prior art, one problem warranting resolution is the single molecule detection of a variety of bioactive agents using DNA hybridization techniques.

SUMMARY OF THE INVENTION

In various representative aspects, the present invention provides a system and method for the single-molecule detection of bioactive agents. In an exemplary application, a molecular rotary motor is attached to a DNA capture probe. A target DNA fragment, suitably adapted for hybridization with said capture probe, may then be provided for hybridization with a DNA signal probe attached to, for example, a fluorescent bead. Measurement of the rotational frequency of the fluorescent bead tethered by the probe sequences is generally selective for specific detection of any bioactive analyte of interest.

Additional advantages of the present invention will be set forth in the Detailed Description which follows and may be obvious from the Detailed Description or may be learned by practice of exemplary embodiments of the invention. Still other advantages of the invention may be realized by means of any of the instrumentalities, methods or combinations particularly pointed out in the claims.

BRIEF DESCRIPTION OF THE DRAWINGS

Representative elements, operational features, applications and/or advantages of the present invention reside inter alia in the details of construction and operation as more fully hereafter depicted, described and claimed—reference being had to the accompanying drawings forming a part hereof, wherein like numerals refer to like parts throughout. Other elements, operational features, applications and/or advantages will become apparent to skilled artisans in light of certain exemplary embodiments recited in the detailed description, wherein:

FIG. 1 generally depicts an exemplary molecular semaphore device in accordance with a representative embodiment of the present invention;

FIG. 2 generally depicts a rotational bio-motor in accordance with a representative embodiment of the prior art;

FIG. 3 generally depicts an exemplary flying head Solid Immersion Microscope (SIM) in accordance with one representative embodiment of the prior art;

Figure 4:
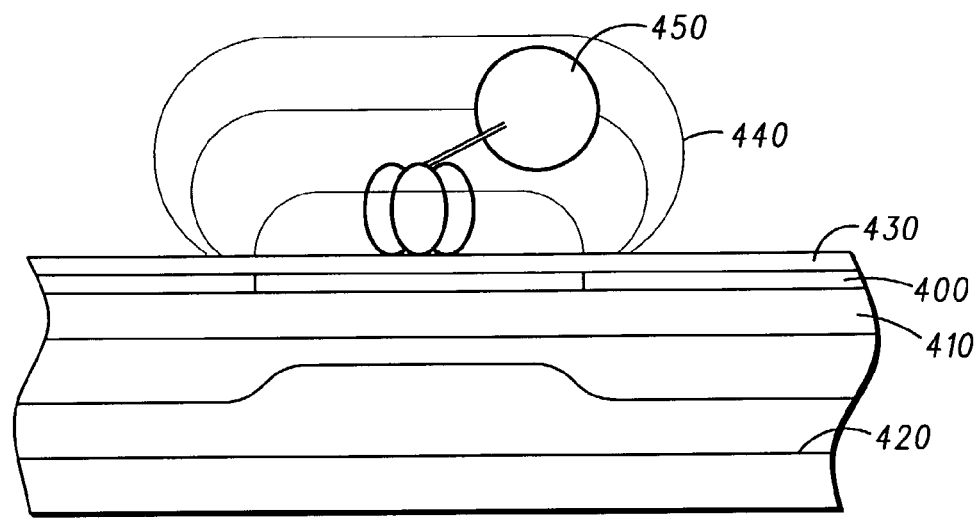
FIG. 4 generally depicts an exemplary SIM suitably adapted for high-speed, high-resolution imaging of molecular semaphore micro-arrays in accordance with a representative embodiment of the present invention.

Those skilled in the art will appreciate that elements in the Figures are illustrated for simplicity and clarity and have not necessarily been drawn to scale. For example, the dimensions of some of the elements in the Figures may be exaggerated relative to other elements to help improve understanding of various embodiments of the present invention.

DETAILED DESCRIPTION OF EXEMPLARY EMBODIMENTS

The following descriptions are of exemplary embodiments of the invention and the inventors' conception of the best mode and are not intended to limit the scope, applicability or configuration of the invention in any way. Rather, the following description is intended to provide convenient illustrations for implementing various embodiments of the invention. As will become apparent, changes may be made in the function and/or arrangement of any of the elements described in the disclosed exemplary embodiments without departing from the spirit and scope of the invention.

Various representative implementations of the present invention may be applied to any micro-array DNA hybridization assay technology. A detailed description of an exemplary application, namely the detection of bio-agents using the F1-ATPase biomolecular motor is provided as a specific enabling disclosure that may be readily generalized by skilled artisans to any application of the disclosed system and method in accordance with various other embodiments of the present invention.

For a general background on biomolecular recognition, detection, spectroscopy, microscopy and velocimetry, see, for example: Dalziel, S. B.; "DigImage-Image Processing for Fluid Dynamics", DL Research Partners Inc., Cambridge, Great Britain (1993); Dracos, Th. and Gruen, A.; *Appl. Mech. Rev.* 51 (6), 387–413 1998); Duggan D. J. et al.;

Nature Genetics 21, 10–14 (1999); Edelstein R. L. et al.; *Biosensors & Bioelectronics* 14, 805–813 (2000); Fritz J. et al.; *Science* 288, 316–318 (2000); Ghosh R. N. and Webb W. W.; *Biophys. J.* 66, 1301–1318 (1994); He L. et al.; *Journal of the American Chemical Society* 122, 9071–9077 (2000); Jenison R. et al.; *Nature Biotechnology* 19, 62–65 (2001); Mansfield S. M. and Kino S. G.; *Appl. Phys. Lett.* 57, 2615 (1990); Nelson B. P. et al.; *Analytical Chemistry* 73, 1–7 (2001); Qian H. et al.; *Biophys. J.* 60, 910–921 (1991); Saxton M. J. and Jacobson K.; *Annu. Rev. Biophys. Biomol. Struct.* 26, 373–99 (1997); Srdic-Mitrovic A. N.; "Interaction of Dense Particles with Stratified and Turbulent Environments", Ph.D. Dissertation, Arizona State University (1998); Steemers F. J. et al.; *Nature Biotechnology* 18, 91–94 (2000); Taton T. A. et al.; *Science* 289, 1757–1760 (2000); Trautman J. K. et al.; *Nature* 40, 369 (1994); Umek R. M. et al.; *Journal of Molecular Diagnostics* 3, 77–84 (2001); Xie X. S. & Dunn R. C.; *Science* 265, 361 (1994); Zenhausern F. et al.; *Science* 269, 1083 (1995).

F1-ATPase is generally believed to comprise the smallest biomolecular motor currently known. It is powered by the hydrolysis of ATP that typically results in rotation about the axis of the γ subunit generally penetrating the core of the enzyme. Rotation of single molecules may often be observed by, for example, fluorescence microscopy. Site-directed mutations of F1 have previously been made to contain histidines (his-tag) at the N-terminus of the F1-α subunits. Due to the high affinity of his-tags for binding with nickel, the enzyme may be fixed to a nickel-coated surface in a unique orientation. Site-directed mutagenesis may then be generally employed to create, for example, a γ subunit cysteine to serve as an anchoring actin filament with attached fluorescent groups. Counterclockwise rotation of the actin, for example driven by ATP hydrolysis, has been observed with fluorescence microscopy.

In one exemplary and representative embodiment of the present invention, a combination of detection of the F1 rotary motor 150 with DNA micro-arrays is disclosed as inter alia increasing the sensitivity and speed of detection of DNA hybridization. Such a device is representatively illustrated in FIG. 1 and may be suitably adapted to detect single molecules of target DNA originating from, for example, a biological warfare agent. The F1-ATPase modified via site-directed mutagenesis to contain his-stranded probe DNA 15-mers (e.g., capture probes) to detect bio-agents is available with modifications for permitting attachment to, for example, the cysteine on the F1-γ subunit. The surface of a slide is generally coated with nickel. The F1-DNA 30-mers are then spotted onto a surface in a micro-array using, for example, ink-jet type delivery such that the his-tags of the F1 bind to the nickel surface with high affinity.

The target DNA 130 of about 30 base pairs from the putative source of bio-agent are then allowed to hybridize with the F1-bound probe DNA 140 on the chip, provided the complementary sequence is recognized. A signal probe 120 is then prepared in advanced for hybridization with the target DNA 130 that was not base-pair matched with the capture probe. Except for the sticky end that recognizes the target DNA 130, the signal probe 120 will generally be double stranded and about 130 base pairs in length. Biotinylation of the distal end may be employed in order to attach, for example, a Streptavidin-labeled fluorescent bead 100 approximately 100 nm in diameter. The length of the signal probe 120 is typically selected to be within the persistence length of dsDNA and will thus provide a substantially rigid tether between F1 150 and the bead 100. After removal of nonspecifically bound target DNA, beads that are nonspecifically bound may thereafter be removed by, for example, washing.

The arrays can be rapidly scanned to identify spots containing the most beads. This inter alia generally identifies the locations where the target DNA has hybridized. The spots may then receive a higher priority for the rotation assay. In the rotation assay, addition of ATP generally induces the rotation of the F1-γ subunit. As the limit of single molecule detection is approached, nonspecific binding of both DNA and beads becomes a significant limitation to detectability. Observation of the rotation of the beads may then be employed to verify that the target is both specifically hybridized to the probe DNA and is attached to the bead; hence the designation of the F1-ATPase as a molecular semaphore. To increase the speed and accuracy of rotational determinations, the assay may optionally be videotaped and analyzed in near real-time by, for example, particle-tracking software.

In accordance with a representative embodiment of the present invention, a sequence-specific nucleic acid hybridization assay is disclosed as capable of detecting at least a single target nucleic acid of interest. The prior art, on the other hand, discloses a linked F1 motor 150 to a BSA 180-coated Au bead 190 through a bio-conjugated immunoassay (biotin 160-streptavidin 170 binding; see, for example, FIG. 2) which is not sequence-specific and thus not suitable for target nucleic acid detection.

Many conventional approaches have been attempted to reduce the detection limit of hybridization in DNA micro-arrays. See, for example, Table 1 vide infra. Direct comparison may often be difficult due in part to method-specific factors between approaches that differ dramatically. Notably, these studies generally differ in the length and sequence of DNA used for hybridization with dissociation constants rarely reported.

Another variable between studies is the identity of the fluorophore used for detection. The detection limit depends inter alia on the fluorescent brightness of the fluorophore and the sensitivity of the instrument. The density of the dye is generally not known such that the detectivity is typically set at the minimum dot fluorescent brightness that may be distinguished from the background when the sensitivity is set so that the brightest element of the sample produces an intensity level at full scale (e.g., signal normalization). The result is that the detection limit is typically determined empirically as the lower limit of the amount of target DNA exposed to the spot containing the probe DNA rather than the number of molecules of hybridized DNA in the spot.

Previously, as few as 600,000 fluorophore molecules could be reliably detected on a 100 $\mu$m diameter spot. Notably, this conventional detection limit is about four (4) times more sensitive than standard commercially available instruments. On average, it may be estimated that about 2.5 million molecules of dye must be bound per spot corresponding to a conventional detection limit.

Arrays are most commonly composed of spots on the order of about 100±50 $\mu$m and require approximately 0.25–1.0 nl of DNA per spot. The density of oligonucleotides bound to the surface of a spot, therefore, is approximately 0.1 pmol per mm$^2$ and 10 pmol per mm$^2$ on glass after ammonia protection and application of aminated polypropylene. For a 100 $\mu$m diameter spot, these densities correspond to about 5E8–5E10 bound oligonucleotides molecules per spot.

TABLE 1

Detection limits of various techniques for DNA hybridization

| Detection method | Detection limit (concentration of target molecules) | Sample Volume | Detection limit (no. of hybridized target molecules) |
|---|---|---|---|
| Fluorescence | 5 pM | 10–50 ul | 1E3 per 100 × 100 um spot |
| "Scanometric" (nanoparticle-based) | 50 fM | | |
| Surface Plasmon Resonance (label-free) | 10 nM | | 6E8 per 500 × 500 um spot |
| Surface Plasmon Resonance (Au-amplified) | 10 pM | | |
| Dye-containing Liposomes | 220 pM | | 6E8 |
| BARC sensor (magnetic beads) | 100 fM (using optical detection) | | |
| Microcantilever Deflection | 400 nM | | 1E10 |
| Molecular Beacons | 100 pM | 10 ul | |
| Electrochemical | 100 pM–100 fM | 500 ul | 1E8 per 100 um pad |
| Optical Interference | 10 fM | 10–25 ul | |

In one exemplary embodiment, in accordance with a representative aspect of the present invention, the surface of glass chips are prepared to comprise a monolayer of nickel tightly bound to the surface to serve as an anchor for the F1-ATPase. Coverslips precleaned with KOH are then immersed in 0.01% acetic acid containing 2% (vol/vol) 3-glycidyloxypropyltimethoxysilane for 3 h at 90° C. and washed with water. The silanated surface is then incubated in 0.01M $NaCO_3$ (pH 10.0) containing 10% (wt/vol) N-(5-amino-1-carboxypentyl)-iminodiacetic acid for 16 h at 60° C. and washed with water. This creates a surface in which nitrilotriacetic acid (NTA) is covalently bound to the surface in a monolayer. Incubation of the surface in 10 mM $NiCl_2$ and 6 mM glycine (pH 8.0) for 2 h at room temperature, then washed with water, typically results in the coordination of about one nickel atom per NTA with high affinity that may be stored in, for example, water until subsequent use.

The nickel is hexa-coordinate and when prepared in this manner, NTA carboxyl groups generally form three ligands to the nickel while the remainder are bound relatively weakly by glycine. Addition of F1-ATPase containing γ subunit-bound DNA-15 mer will typically bind quite tightly to the surface of the slide due to the presence of the his-tags. Each of the three F1-α subunits may typically have an extension of six histidines. The imidazole groups of this amino acid coordinate with the nickel displacing glycine and thereby become bound to the surface by as many as eighteen nickel atoms.

The F1-ATPase-DNA 15-mers may generally be applied to the surface with an ink jet delivery system. Deposition typically employs 50 μm diameter spots corresponding to the field of view of the microscope used for the detection of rotation. This may be a significant consideration inasmuch as the detection system may generally be optimized when the majority of spots are in the field of view in order to detect substantially each possible hybridization event. The field of view may also be defined by the magnification of the image necessary to resolve rotation of the bead attached to the F1-γ subunit.

The length of the DNA tether and the size of the fluorescent bead may generally be chosen to optimize detection of rotation by, for example, a particle-tracking system. In order to be detectable, the rotation must usually involve sufficient displacement of the centroid of the particle image (a few pixels at minimum), and the rotation rate must generally be less than one-half the frame rate of the camera. While these factors favor the use of a relatively long tether (and large bead), the length of the tether is generally limited by inter alia the mechanical properties of DNA. DNA exhibits at least two distinct regimes of mechanical behavior, depending on whether the length of the molecule is greater or less than the persistence length, which for dsDNA is approximately 150 bps or about 50 nm. For contour lengths less than the persistence length, dsDNA behaves as a substantially semi-rigid rod. For contour lengths much greater than the persistence length, it behaves similar to a wormlike chain. A bead attached by such a flexible tether may be strongly influenced by, for example, Brownian forces and weakly driven by the F1, making detection of rotation difficult. For these reasons, in one representative and exemplary embodiment of the present invention, a 150-mer tether may be employed with a 100 nm diameter bead.

It is noteworthy that a comparable 50 μm diameter spot for a conventional micro-array would be expected to contain between about 1E8 and about 1E10 bound oligonucleotides molecules per spot. Of these, a significant fraction would generally need to be hybridized with target DNA in order to render themselves detectable. Although there may be several thousand F1-ATPase molecules, each with a capture probe attached, only the rotation of one need be observed in order to confirm that a hybridization event in fact has taken place.

The $F_1F_0$ ATP synthase has nearly universal importance among all life forms as a source of biological energy in the form of ATP. In living things, this enzyme uses a trans-membrane proton gradient derived from the oxidation of metabolites to drive the reaction ADP+Pi$\leftarrow\rightarrow$ATP+$H_2O$ beyond the point of equilibrium, and thereby maintain high cellular concentrations of ATP. Many enzymes use the energy gained by ATP hydrolysis to return the ATP/ADP*Pi chemical gradient toward equilibrium in order to catalyze other reactions. Under some conditions, this enzyme may catalyze ATP hydrolysis in order to pump protons in the reverse direction across the membrane.

The intrinsic membrane Fo protein complex generally mediates proton translocation. The extrinsic membrane F1 protein complex may be solubilized from the membrane where, in the absence of Fo, it catalyzes ATP hydrolysis. Partial structures of soluble F1 have been determined from bovine mitochondrial F1, rat liver mitochondria, thermo-phillic *Bacillus* PS3, *E. coli* and $F_1F_0$ from yeast. The three α and three β subunits, which fold in a similar manner, are arranged alternately like segments of an orange around a large portion of the γ subunit. The binding sites for the nucleotides are generally at the interfaces between α and β subunits. The catalytic sites are predominantly in the β subunits with some contributions from groups on the α subunits and conversely with the non-catalytic sites. This core of the 'orange' contains a coiled-component composed of the N and C termini of the γ subunit. The remainder of the γ subunit is generally bound to the ε subunit that protrudes from the core of the 'orange' in a stem-like structure. This stem generally serves as an interface with the Fo complex.

The observation that ATPase activity in soluble F1 causes the rotation of the γ subunit provides insight to questions concerning how the catalytic subunits act cooperatively and how the energy of the proton gradient may be exploited to make the conformational changes in the F1 complex. In the most compelling demonstration, of γ rotation, an actin filament configured with fluorescent groups was attached, to the γ subunit of F1. Counterclockwise rotation of the actin driven by ATP hydrolysis was observed with a fluorescence microscope. In F1 from bovine mitochondria, three catalytic sites are asymmetric in that one contains bound $Mg^{2+}$-ADP ($\beta_{DP}$), one contains bound $Mg^{2+}$-AMPPNP (an analog of ATP) ($\beta_{TP}$) and one is empty ($\beta_E$). Such asymmetry was previously predicted from experiments that served as the basis of the binding-change hypothesis. In this hypothesis, the enzyme adopts a conformation at one of the three catalytic sites in which ADP and phosphate are relatively tightly bound. In this high affinity conformation, the equilibrium of the ADP+Pi$\leftarrow\rightarrow$ATP+$H_2O$ reaction is near unity; accordingly, the synthesis of ATP is not generally considered to be the rate-determining step. Instead, input of energy from the proton gradient may be employed to drive conformational changes that inter alia promote the release of newly synthesized ATP. The conformation of catalytic sites was originally believed to be staggered and to work in a cooperative manner since this conformational change may generally only be observed when an adjacent empty catalytic site fills with substrate. Consequently the F1-ATPase behaves as a three-piston rotary motor. Based on the direction of γ rotation, the sequence of conformations of each catalytic site corresponding to the transition series: $\beta_E \rightarrow \beta_{TP} \rightarrow \beta_{DP} \rightarrow \beta_E$ during ATP hydrolysis.

The asymmetry of the catalytic sites generally necessary for the binding-change mechanism typically depends on the γ subunit and $Mg^{2+}$. In the absence of the γ subunit and $Mg^{2+}$, the crystal structure of the $\alpha_3\beta_3$ complex from thermophillic *Bacillus* PS3 has three-fold symmetry as does the rat liver structure crystallized in the absence of $Mg^{2+}$. The $Mg^{2+}$-induced asymmetry of the catalytic sites is also believed to be responsible for the differences in nucleotide affinity between these sites. Using the βY331W mutant in *E. coli* F1, previous researchers were able to monitor the catalytic site occupancy for the quenching of tryptophan fluorescence that occurs when the nucleotide is bound. In the absence of $Mg^{2+}$, the three catalytic sites bind ATP with substantially the same affinity. However, when ATP binds as a complex with $Mg^{2+}$, the affinity for nucleotides may differ by as much as about five orders of magnitude.

Magnesium may often be difficult to study due to the lack of spectroscopic probes and may also be difficult to identify in a protein crystal structure because it has a similar size and electron density as that of water. At least one investigation was previously undertaken to identify the metal ligands that orient the $Mg^{2+}$-nucleotide complex in the catalytic site. Vanadyl $(V^{IV}=O)^{2+}$ generally provides a direct probe of the types of groups that typically serve as ligands to the F1 metal cofactor because the A and g tensors of $^{51}V$ hyperfine couplings from the EPR spectrum of the bound $VO^{2+}$ generally correspond to a measure of the nature of the equatorial metal ligands. Identification of specific residues as metal ligands were made by analysis of the changes in the $^{51}V$-hyperfine EPR parameters of enzyme-bound $VO^{2+}$ induced by site-directed mutations of each metal ligand.

In one representative and exemplary embodiment of the present invention, a method for the reliable observation of the rotary motion of the F1-γ subunit driven by ATP hydrolysis is disclosed. Single molecule rotation has been observed by attachment to the γ subunit of either an actin filament or a bead visible by, for example, optical microscopy. The rotation rate, like the maximal rate of ATP hydrolysis, generally depends on ATP concentration, but typically does not increase at concentrations above about 2 mM.

Frictional drag on the γ subunit may limit the rate of rotation. It has been determined that a 40 nm diameter bead generally does not provide sufficient drag to serve as an impeding load. The full speed of the F1 motor measured at 2 mM ATP with a 40 nm bead as a probe is about 134 rps (revolutions per second) at 23° C. With an actin filament 1 μm in length attached, the maximal rotation rate at 2 mM ATP is about 4 rps. The corresponding torque on the γ subunit generated by the hydrolysis of ATP is approximately 40 pN nm. Rotation may typically be sustained for on the order of tens of minutes and has been observed for more than 2 hours.

At sub-saturating ATP concentrations, the ATPase rate may be inhibited by the tight binding of Mg-ATP to F1. The hydrolysis rate is generally suppressed the greatest at 50 μM ATP. Saturating concentrations (i.e., 2 mM ATP) generally do not present a problem inasmuch as ATP can bind to the non-catalytic sites on the α subunits in a manner that prevents Mg-ADP inhibition. This inhibition may also be prevented by 10–30 mM lauryldodecylamine oxide (LDAO). The maximum speed of rotation at saturating ATP concentrations is generally not affected by the presence of this detergent.

Solvents like ethanol, methanol and the like may also increase the activity of F1 from many organisms when present in concentrations of about 20–25%. The decreased polarity of the solvent generally decreases hydrophobic interactions that involve the ε subunit. This subunit has been referred to as the ATPase inhibitor protein because in F1Fo, it is believed to foster ATP synthesis at the expense of ATP hydrolysis. Since F1Fo is a membrane protein, it is relatively tolerant to a variety of detergents and surfactants.

F1 is viable at 55° C. with rates of ATP hydrolysis increasing up to that temperature. The enzyme is generally slowly inactivated at 4° C. and, is thus typically kept at room temperature for short-term storage. Long-term storage may be achieved in a liquid nitrogen dewar or in a −80° C. freezer. In the former, various exemplary embodiments of the present invention have demonstrated that the enzyme retains its original activity for years. The oldest samples examined in this regard were at least 5 years old. The enzyme stored in a −80° C. freezer was observed to remain stable for at least 6 months if stored in an aqueous solution of 30% glycerol. Over the past two decades, the enzyme has been studied as purified from spinach, wheat, *Chlamydomonas reinhardtii, Escherichia coli* and thermophillic bacteria PS3. Each of these has minor differences with respect to the conditions that promote stability. In one exemplary embodiment, in accordance with a representative aspect of the present invention, *E. coli*-F1 was used. However, skilled artisans will appreciate that various other enzymes from other sources may be employed inter alia to increase temperature stability of the enzyme, etc.

Rotation of the γ subunit was detected with a 40 nm bead when the bead was attached obliquely to the axis of rotation. A sulfydryl group in the γ subunit was engineered using site-directed mutagenesis to covalently react with, for example, biotin maleimide. Streptavidin, with its multiple high affinity binding sites for biotin, was then anchored specifically at this location. Single stranded DNA 30-mers were also biotinylated in order to bind F1 via Streptavidin. Sited-directed mutagenesis was also employed to extend the α subunit N-terminus by 6 histidine residues to create a his-tag. Nickel generally has a high affinity for his-tags that enables the F1 to bind to nickel dots deposited on the surface of an assay chip. This binding generally positions the enzyme with the single stranded probe DNA away from the chip surface and with the axis of rotation normal to the surface. The his-tag also dramatically simplifies the purification of the enzyme from the bacteria.

In another exemplary embodiment, in accordance with a representative aspect of the present invention, F1 may be bound to a coverslip for use in rotation assays, but effectively cut to dimensions permitting it to be inserted into, for example, a spectrophotometer. Using a coupled assay comprising pyruvate kinase and lactic dehydrogenase, the ATPase activity of the coverslip-bound F1 may be measured. Skilled artisans will appreciate that substantially higher sensitivity may be achieved by using inter alia assay chips comprising a grid of, for example, 50 nm diameter nickel dots where the total number of dots is generally known. Accordingly, it becomes straightforward to assess the ATPase activity of the chip-bound, bead-containing F1 with the coupled assay.

Typical DNA hybridization conditions for micro-arrays may comprise approximately 14–18 hours in 3×SSC (450 mM NaCl, 45 mM NaCitrate, pH 7.0) at 42° C. The samples sometimes may also further comprise a small amount (0.03%) of sodium dodecyl sulfate (SDS) that may be optionally omitted. The chips may then be given washes in 2×SSC, 1×SSC and 0.2×SSC. These conditions generally are rendered compatible with the F1-ATPase so as to maintain the viability of the enzyme as an ATPase-driven rotary motor for the detection of hybridization.

The F1-ATPase activity is generally observed to be stable between pH 7–8 and with the highest concentrations of NaCl and NaCitrate used during hybridization typically not effecting activity. In fact, the enzyme may be purified by the use of solutions containing similar salt concentrations. Moreover, the enzyme is generally stable at these temperatures as well.

Typical libraries of bio-agents include, for example:

| Type | bio-agents |
|---|---|
| Bacteria | Anthrax, Plague, Cholera, Tularemia, Q Fever, Brucellosis, E. Coli |
| Virus | Smallpox, Viral Encephalitides, Hemorrhagic Fever |
| Toxins | Staphylococcal Enterotoxin B, Ricin, Botulinum Toxin, Mycotoxins |

In one exemplary embodiment of the present invention, the hybridization array from E. Coli genomic DNA amplicons may be employed. In another exemplary embodiment of the present invention, integration of the upstream sample prep, such as preconcentration and/or separation of pathogens from body fluids and/or environmental samples, is disclosed.

Exemplary methods for the preparation of single-stranded target DNA may include:
(1) ssDNA preparation from Streptavidin coated magnetic beads (DYNAL). The ds amplicon generally has biotinylated strands for capture onto Streptavidin beads.

The following exemplary method details one representative procedure for the preparation of fluorescein-labeled dsDNA in accordance with the present invention:
1. Use biotinylated (reverse/forward) and fluorescein-labeled (forward and/or reverse) primers to perform PCR. Each primer may have more than one fluorescent dye; and
2. Use F-dNTP (Molecular Probes, F-dUTP), along with biotin-primer and/or fluorescein-primer to perform PCR.

Then every A, T has a fluorescein→250 fluoresceins/1 kb. The nucleotides should include: dATP, dCTP, dGTP and F-dUTP.

Pre-wash of Dynal beads:
1. Re-suspend beads by gently shaking the vials (rigorous shaking generally strips the Streptavidin from the surface);
2. Transfer 100 µl Dynal beads to a tube;
3. Employ magnetic separator until solution is substantially clear;
4. Aspirate supernatant and discard;
5. Add 200 µl pre-wash buffer (TE1000);
6. Re-suspend the beads by mixing;
7. Place the tube in the separator until solution is substantially clear;
8. Aspirate supernatant and discard; and
9. Add 100 µl capturing buffer (TE1500).

Capture:
10. Add 50 µl PCR product and mix gently;
11. Incubate at least 15 minutes with substantially continuous agitation (tap the tubes);
12. Place in separator until solution is substantially clear;
13. Remove supernatant (save to make sure that the sample binds to the beads); and wash a few more times.

Elution by denaturation:
14. Add 20 µl melting solution (0.1 N NaOH) to the beads;
15. Vortex intermittently for 5 minutes;
16. Place in separator until solution is substantially clear;
17. Transfer supernatant to fresh tubes containing 10 ul of 0.2M HCl; and
18. Neutralize the ssDNA using buffer.

Thereafter, the ssDNA generally contain fluorescein dyes.

Alternately, one may perform Tm-biased or strand-biased PCR so that inter alia the single stranded product may be more pre-dominant than the double-stranded one and ready for hybridization. In this case, magnetic bead separation may not be required.

The experimental validity of the strand-biased PCR has been demonstrated here by amplifying Human cytochrome P450 (CYP17, 161 bp) gene to yield a more pre-dominant ssDNA product than the dsDNA for SNP detection. This may be accomplished, for example, by using about 10 times more reversed (R') primers than forward (F') primers so that the forward primers will be depleted first in the PCR reaction, leaving the reversed primers duplicating the biased strand. Single-stranded DNA was verified using an Agilent Bioanalyzer 2000 in which the ssDNA band was generally not detected. The PCR product was then loaded without substantial further purification with hybridization buffer into a Motorola® eSensor® chip (available from Motorola®; Schaumburg, Ill., USA) for electrochemical detection of SNP.

Biotinylated sample DNA was then applied to the molecular semaphore chip and allowed to hybridize with complementary probe DNA. Non-specifically bound DNA was thereafter removed by washing. Next, Streptavidin-coated fluorescent nanospheres are introduced and allowed to bind to sample DNA that had at least partially hybridized with F1-bound probes DNA, such that each hybridized DNA pair acts as a tether linking a fluorescent bead to the γ subunit of an F1 motor. Detection of hybridization events are generally obtained by means of rotation assay. In such an assay, ATP is added to the solution to induce rotation of the γ subunits of the motors. As a result, a fluorescent bead attached to one of the γ subunits via, for example, a hybridized DNA tether will (provided the tether is sufficiently rigid) generally tend to rotate in a periodic manner about the motor. Using particle tracking, the trajectory of a tethered bead rotating in such a fashion may be readily distinguished from the trajectory of a bead that is either free-floating or non-specifically bound to the surface of the chip. The detection of bead rotation thus provides an effective discriminator for the attachment of the bead to an F1 motor and, by extension, for the presence of a hybridized DNA pair.

The motion of particles tethered to single molecules of DNA has previously been investigated both experimentally and theoretically. Whereas the particles in previous studies were generally tethered to immobile substrates and driven by Brownian forces, the nanospheres bound to F1 motors are typically acted upon both by Brownian forces and by the force transmitted to them from the motors via the DNA tethers. The motion of the nanospheres is generally governed by the interplay of these forces and depends at least partly on the mechanical properties of the tether. Double-stranded DNA is known to behave as a relatively weakly bending beam for lengths less than the persistence length (about 150 bp or about 50 nm) and as a wormlike random coil for lengths substantially greater than the persistence. If the tether is substantially shorter than the persistence length, simple analytic models may be used to approximate the motion of the bead, given the known torque and/or angular velocity characteristics of the F1 motor. If the tether is longer than the persistence length of dsDNA or if a portion of the tether is single-stranded, no simple analytical models generally exist and Brownian dynamics simulations may be employed to analyze the motion of the bead. If the DNA tether is sufficiently short then it may generally be assumed to comprise a rigid rotor; the rotation rate of the attached microsphere being approximated from the known performance characteristics of the F1 motor and the viscous drag of the bead-tether assembly.

Performance characteristics of the F1 motor have previously been investigated by attaching particles ranging from actin filaments to micro/nanospheres to nanofabricated metal propellers to the γ subunit of a substrate-bound F1 and then observing the rotation rate as the particle size, and hence the viscous drag, is varied. At low (e.g., $\mu$M) ATP concentrations, the rotation rate of the motor is generally diffusion limited. Under saturating (mM) ATP conditions, the F1-ATPase exhibits at least two motion regimes: a constant torque regime at moderate to high loads and a constant velocity regime at low loads. For a particle with drag coefficient ξ, the rotation rate may be described by the following empirically derived expression:

$$f = \left(\frac{1}{f_{noload}} + \frac{2\pi\xi}{N}\right)^{-1}$$

where $f_{noload}$ is the rotation rate of the unloaded motor and N is the torque constant of the motor, equal to approximately 40 pN nm.

The drag coefficient of a cylinder of length L and radius b rotating about one end in an unbounded liquid of viscosity η may generally be expressed as:

$$\xi_{cyl} = \frac{\frac{4}{3}\pi\eta L^3}{\ln\left(\frac{L}{2b}\right) - 0.447}$$

The drag coefficient of a sphere of radius a rotating, as if connected by a rigid rod about an axis located a distance R from its center in an unbounded liquid of viscosity η may generally be expressed as $\xi_{sphere}=8\pi\eta a^3+6\pi\eta R^2 a$. Neglecting hydrodynamic interactions between the rod and the sphere, the combined rotational drag coefficient for the rod-sphere assembly may be approximated as:

$$\xi = \frac{\frac{4}{3}\pi\eta L^3}{\ln\left(\frac{L}{2b}\right) - 0.447} + 8\pi\eta a^3 + 6\pi\eta(L+a)^2 a$$

Using these equations, the rotation rate for a bead of a give size attached to a tether of a given length may be determined.

A single-particle tracking (SPT), computer-enhanced video microscopy method may be used to track the motion of proteins or lipids on, for example, a cell surface. Individual molecules or small clusters may be observed with a typical spatial resolution of tens of nanometers and a typical time resolution of tens of milliseconds. This method was used to measure the motion of membrane components and resolve modes of motion of individual molecules. Of particular and notable comment, the use of the SPT technique demonstrated that motion in the membrane is not limited to pure diffusion. By analyzing trajectories of individual molecules, several modes of motion have been observed: immobile, directed, confined, tethered, normal diffusion, and anomalous diffusion.

A similar method may be borrowed from fluid dynamics for measuring Lagrangian velocity fields. In a preferred exemplary embodiment, in accordance with a representative aspect of the present invention, a particle-tracking system called DigImage (available from D. L. Research Partners; UK) has been used for various measurements. The system is based on recording a flow to videotape with, for example, a CCD camera and subsequently digitizing and analyzing the acquired images. The data acquisition board has a resolution on the order of 512×480 pixels and 1 byte image depth. This automated tracking program generally enables 4096 particles to be recognized simultaneously, precisely located and tracked though a virtually unlimited number of images without the need for user interaction. The position of each particle is generally defined as the centroid of its intensity (determined from the spatial mean of pixels occupied by the particle weighted by the intensity of each of those pixels) with typical accuracy achieved in locating particles on the order of about 0.1 pixels. The tracking algorithm is based on a transportation algorithm in which the solution may be obtained by characterizing a minimum of a prescribed cost function as described, for example, vide infra. The digital data corresponding to the coordinates of each particle versus time are also available for a variety of further analyses—typically resulting in the determination of the Lagrangian statistics of the particle's motion.

One representative and exemplary application generally involves detecting the rotation of certain particles in a field of view (50 $\mu$m×50 $\mu$m) in which a relatively large number of particles are visible and typically exhibit different modes of motion: i.e., Brownian motion (e.g., free floating particles), immobile (e.g., particles that bind nonspecifically to the surface) and rotation corrupted by Brownian motion (e.g., nanospheres attached to bound target sequences). In order to distinguish between rotation and other modes of the motion, individual particle trajectories generally are obtained with the Lagrangian spectra of those trajectories analyzed by a peak detection algorithm to capture the corresponding rotation frequency (in the absence of rotation the spectra will generally be proportional to $$\frac{1}{\omega^2},$$

where ω is the frequency of motion).

In accordance with a representative embodiment of the present invention, a system was used to obtain video recordings of the motion of 1 μm beads attached to the F1. Individual trajectories were obtained and their Lagrangian spectra were determined. The spectra demonstrated a distinct peak at a frequency of about 2 Hz corresponding to the expected rate of the rotation of F1 loaded with a 1 μm bead.

In an exemplary embodiment of the present invention, the size of the particles and curvature of their trajectories (on the order of about a few tens of nanometers) are quite small in comparison to the field of view (on the order of about 50 μm). In general, a reliable system for detection of rotation, in accordance with an exemplary and representative embodiment of the present invention, generally comprises much better resolution than 510×480 pixels and, given that CCD cameras of higher resolution and higher image depth are currently commercially available, the present invention also embodies a computer program for particle tracking for inter alia this particular application.

The particle-tracking program generally operates on digital images of arbitrary size and image depth and acquired at arbitrary frame rate. Such features generally offer the following advantages: (i) elimination of the video recorder for the system substantially contributes to the improvement of the signal-to-noise ratio as well as the accuracy with which particles may be located; and (ii) software based on analyzing images of arbitrary size and depth acquired at arbitrary frame rate also enable utilization of the full range of the available spatial and temporal resolution of the hardware as well as the potential for improving the performance of the system without changing the software. For example, the time required to analyze each sample may be a constraint for certain practical applications and is mainly determined by, for example, rate of rotation (e.g., the trajectory should contain a certain number of revolutions in order to yield a distinct spectral peak) and should be approximately 1000 images long in order to produce a smooth correlation. Given that rate of rotation of F1 may be 20 revolutions per second, only a few seconds of recording may satisfy the first requirement; but if a standard-rate CCD camera is used, acquisition may need to be at least 30–40 seconds long in order to provide a sufficient number of images in the sequence. Thus, use of a high-speed camera would be expected to significantly reduce the time needed to analyze one patch providing that the fluorescent labels used may be recorded over the exposure time associated with the specific frame rate.

The analysis of images aimed at the representative detection of rotating particles may be divided into the following exemplary steps:
  (i) Determination of particle positions in images;
  (ii) Tracking particle positions in time; and
  (iii) Obtaining Lagrangian spectra of individual trajectories and applying peak detection algorithm(s) in order to detect corresponding rotational frequencies.

Various techniques may be applied to determine locations of particles in images. In order to obtain subpixel accuracy however, images of particles may need to be a few pixels in size and if that condition is satisfied most of the methods applied will result with accuracy on the order of 0.1 pixels in determining particle location.

One of the simplest methods for determining particle image coordinates involves a grey-level center of gravity algorithm where $x_i, y_i$ are the coordinates of pixel i in the image of a particle and $g_i$ its grey-level according to:

$$x_p = \frac{\sum g_i x_i}{\sum g_i}$$

$$y_p = \frac{\sum g_i y_i}{\sum g_i}$$

Application of this algorithm on images containing a sufficient number of pixels (on the average 12 pixels; e.g., 3 pixels×4 pixels) and exploiting a significant portion of the gray-level range (say 20% for 1 byte depth of image) generally allows determination of the image coordinates of particles with an accuracy on the order of about 0.1 pixel. An alternative method to locate particle positions comprises fitting Gaussian shape function(s) on the image area where local intensity maxima are detected. This method is generally able to resolve overlapping particle images but often requires longer computational time than the gray-level center of gravity method.

Particle tracking in time generally involves connecting an image or object's special coordinates of a given particle through sets of coordinates obtained at different instants. Accordingly, the system may be cast as an assignment problem, which mathematically is analogous to a transportation problem which may be stated as follows:

Two sets may be considered—set $S_1$ containing m elements and set $S_2$ containing n elements. The number of elements m in set $S_1$ is not necessarily equal to the number of elements n in set $S_2$. The optimal set of associations $A=\{a_{ij}\}$ is to be found. The set of associations is optimal in the sense that it minimizes or maximizes an objective function, for example:

$$O = \sum_{i=1}^{m}\sum_{j=1}^{n} c_{ij} a_{ij}$$

where $c_{ij}$ is a given cost of associating element i from set $S_1$ and element j from set $S_2$. The solution to be found is generally subject to the following constraints:

$$\sum_j a_{ij} = a_i$$

$$\sum_i a_{ij} = b_j$$

$$a_{ij} > 0$$

where $a_i$ is the number of elements of type i and $b_j$ is the number of elements of type j used in the calculation of the cost function.

The transportation problem applied to particle tracking in time may be formulated as two assignment problems. Sets of particle coordinates obtained at three consecutive instants are considered, say set I={$p_i$; i=1; M} obtained at $t_{n-1}=t_n-\Delta t$, set J={$p_j$; j=1; N} obtained at $t_n$ and set K{$p_k$; k=1; L} obtained at $t_{n+1}=t_n+\Delta t$. The particles' trajectories may be obtained by solving two assignment problems.

The first assignment problem involves relating positions of particles in set J and positions of particles in set K, thus relating the instants t=$t_n$ and t=$t_{n+1}$. The optimal set of links L={$l_{jk}$} may be found by minimizing an objective function:

$$O = \sum_{k=1}^{M}\sum_{j=1}^{M} c_{jk} l_{jk}$$

where $c_{jk}$ is the cost of association of the location of the particle $p_k$ from the set K and location of particle $p_j$ from the set J defined as:

$$c_{jk} = \frac{|X_j + u_j \Delta t - X_k|}{\varepsilon_{max}} c_{max}.$$

Here, $X_k$ is the position vector of particle $p_k$ from the set K and $X_j+u_j\Delta t$ is the predicted position vector of the particle $p_j$ from the set J in the set K based on the velocity $u_j$ obtained in the previous step. The maximum matching distance allowed is $\varepsilon_{max}$ and $c_{max}$ is the maximum value of the cost of association.

The solution may be found subject to the following constraints:

$$\sum_k l_{jk} = 1$$

$$\sum_j l_{jk} = 1$$

$$l_{jk} > 0$$

Thus, the objective function may be defined so as to force the solution to the location of the particle nearest to the position predicted by the velocity obtained in the previous time step. The constraints provide a solution substantially free of multiple connected trajectories.

The second assignment problem may be employed to improve continuity of trajectories and is generally defined among the sets I and K. If the particle location k in set K is not related to any particle in set J, then an attempt is made to establish the missing link with some of the unconnected particles in set I that had a velocity history. Thus, the algorithm reverses two steps back in time in order to provide uninterrupted trajectories even if the position of the particle had not been obtained in one time step.

In order to distinguish between rotation and other modes of the motion, the Lagrangian spectra of trajectories may be analyzed. The Lagrangian spectra of particle velocity may be evaluated as the cosine Fourier transform of the Lagrangian autocovariance $R^L(\tau)$:

$$E^L(\omega_n) = \frac{1}{N}\left[2\sum_{k=1}^{N} R^L(k\Delta t)\cos(\omega_n k \Delta t) + R^L(0)\right]$$

where $$R^L(\tau) = <v(t)v(t+\tau)>$$

$$\omega_n = \frac{\pi n}{N}\Delta t$$

n=1,N

The particles exhibiting Brownian motion and those rotating with a certain frequency will generally have very different forms of the Lagrangian spectra: velocity spectra of Brownian motion will typically be proportional to $$\frac{1}{\omega^2},$$

where ω is the frequency of motion, and rotation will typically be observed as a spike at the rotational frequency which will be superimposed on the $$\frac{1}{\omega^2}$$

portion of the spectra.

Validation of the tracking procedure using real data may be impossible due inter alia to the data generally being corrupted by an unknown level of noise introduced during recording and digitizing. Thus, the tracking algorithm may be tested by generating a set of synthetic data explicitly corrupted by a controllable (e.g., known) type and amount of noise. These data may comprise, for example, a set of images, a set of particle coordinates and/or the like. Testing of the algorithm on a set of artificial images provides an opportunity to quantify effects of various sources of noise on the performance of the methodology. A number of particles will generally be randomly distributed in the initial image. Thereafter, the sequence of artificial images may be created by prescribing different types of motions to the particles in the initial image: some particles may be caused to rotate with a prescribed rate of rotation and that rotational motion will generally be corrupted by a certain level of randomness. Some particles will be immobilized and some will exhibit Brownian motion. Also, different types and different levels of noise may be added to the images in order to test the robustness of the process and its ability to tolerate inter alia noise arising from the limited stability of the apparatus or produced by, for example, the CCD chip itself. The parameters to be varied in order to establish a measure of reliability of the method include, but are not limited to: ratio of rotational frequency and frame rate; level of randomness superimposed on the rotation; length of image sequence; type and level of noise superimposed on the entire image sequence; etc.

While the molecular semaphore micro-array may be scanned using conventional optical scanners, the throughput and spatial resolution is often quite limited. In accordance with another exemplary embodiment of the present invention, a high-speed and high-resolution optical scanning system is disclosed for fast read-out and high S/N detection of, for example, rare bio-warfare agents. An exemplary system, as representatively depicted for example in FIG. 4, comprises inter alia a flying-head solid immersion microscope (SIM) typically used as an optical head for optical storage systems. The SIM has a minimal readout speed on the order of about 40 MHz for optical microscopy and generally employs a standard or confocal optical microscope to focus the light beam onto a lower surface of a high refractive index solid transparent material 310 (i.e., Ni/Cr) acting as a solid immersion lens 325 (SIL). The SIM uses the effective shorter wavelength inside a medium to give a smaller spot size and better resolution. This allows structures to be resolved down to about 50 nm, comparable to similar detection techniques such as, for example, the scanning near-field optical microscope (NSOM) and the scanning interferometric apertureless microscope (SIAM).

FIG. 3 illustrates an exemplary flying head Solid Immersion Microscope (SIM) in accordance with one representative embodiment of the prior art. The main components comprise: a laser 200; objective lens 210; flying head 220; solid immersion lens 230; polymeric substrate 240; evanescent coupling region 250; first surface recording (i.e., top of substrate) 260; lens/substrate spacing controlled by flying head 270; and magnetic coils 280.

A preferred embodiment to detect the motion of said molecular semaphore comprises an optical microscope similar to a scanning near-field microscope, like the NSOM described into U.S. Pat. No. 5,389,779 issued to Betzig et al. or an apertureless microscope as described into U.S. Pat. Nos. 5,623,338; 5,624,845; 5,602,820 issued to Zenhausern et al. A photon tunneling imaging system, as described in the prior art by Guerra (Applied Optics, 29, 26, 1990, 3741–3752) that can create evanescent fields could also be applicable to detect the motion of fluorescent beads attached to a biomolecule. However, the present invention is directed to its practice using an array of biomolecular semaphores for which the implementation of a near-field optical means that can operate some fast three dimensional motion on at least the size of a few arrays is preferred. It is within the scope of the present invention to report a further improvement over the prior art, and in particular in reference to the experimental setup reported in the literature by Terris et al. (Appl. Phys. Lett., 65, 4, 1994, 388–390), and that can be described by the use of a near-field flying head system that can operate in a differential illumination mode by preferably combining a Nomarski prism and a solid immersion lens (SIL). The diagram of FIG. 4 represents such a preferred embodiment. The main components comprise: 300 index matching oil (n>1); 305 liquid such as biological buffer or aqueous based solution; 310 transparent substrate with preferably Ni/Cr islands to perform the appropriate surface chemistry attachment of said nanomotor; 315 microfluidic channel or chamber; 320 air-bearing spindle; 325 solid immersion lens; 330 slider; 335 suspension means; 340 signal beam; 345 reference beam; 350 Wollaston or Nomarski prism; 355 polarizer; 360 interferometer such as Michelson or any other interferometric systems known by those skilled in the art; 365 optical pick-up feedback; 370 focusing servo; 375 coherent light source such as LED, laser and a photodetector such as photodiode or the like; 380 air/liquid gap servo mixture.

Figure 5:
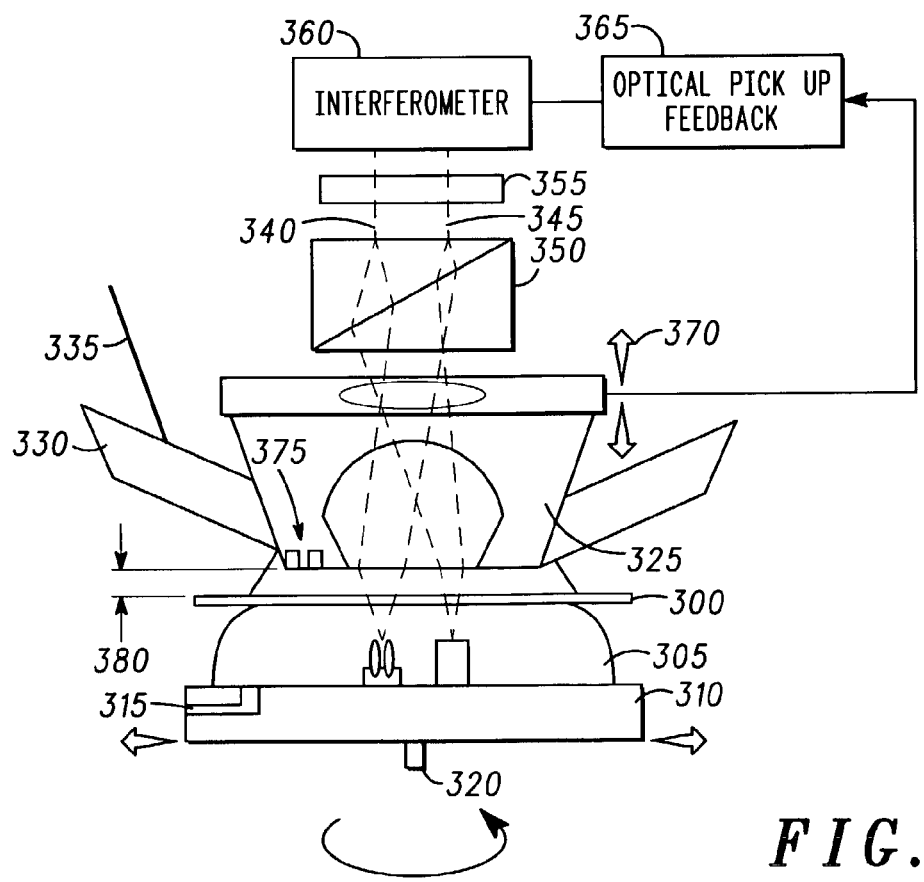
FIG. 5 generally depicts an exemplary near-field excitation system suitably adapted for high S/N imaging of molecular semaphore micro-arrays in accordance with yet another representative embodiment of the present invention.

To increase the S/N ratio and therefore the detection sensitivity of said molecular semaphore, a near-field excitation with evanescent waves to the reporter 100 is preferred. A preferred embodiment, shown for example in FIG. 5, comprises a near-field aperture 400 fabricated on a transparent substrate 410, such as quartz glass, and a thin insulating layer 430 to cover the aperture 400 to prevent it from reacting to the bio reagents used for hybridization. The planar excitation wave 420 is to be modulated by the near-field aperture 400 which leaves only the evanescent wave to penetrate the aperture 400 to excite the F1 motor rotary assay 450. By this embodiment, the contribution of noise due to the far-field excitation wave will be greatly minimized.

The present invention may be described herein in terms of various processing steps. It should be appreciated that such processing steps may be realized by any number of hardware and/or software components configured to perform the specified functions. For example, the present invention may employ various integrated circuit components, e.g., memory elements, processing elements, logic elements, matchable data structures, and the like, which may carry out a variety of functions under the control of one or more microprocessors or other control devices.

Similarly, the software elements of the present invention may be implemented with any programming or scripting language such as, for example, Fortran, HPFortran, C, C++, Java, COBOL, assembler, PERL, eXtensible Markup Language (XML), etc., or any programming or scripting language now known or hereafter derived in the art, with the various algorithms being implemented with any combination of data structures, objects, processes, routines or other programming elements. Further, it should be noted that the present invention may employ any number of conventional techniques for data transmission, signaling, data processing, parallelization, distributed processing, network control, and the like. Still further, the invention may employ various security measures to prevent or otherwise deter, for example, code de-compilation with inter alia client-side scripting languages, such as JavaScript, VBScript and/or the like. Alternatively, conjunctively or sequentially, the present invention may also employ cryptographic features designed to protect access to data files and/or de-compilation of executable code. For a basic introduction of cryptography, please review, for example, the text written by Bruce Schneider entitled "Applied Cryptography: Protocols, Algorithms, And Source Code In C," published by John Wiley & Sons (second edition, 1996).

It should be appreciated that the particular implementations shown and described herein are illustrative of the invention and its best mode and are not intended to otherwise limit the scope of the present invention in any way. Indeed, for the sake of brevity, conventional data processing, application development and other functional aspects of the systems (and components of the individual operating components of the systems) may not be described in detail herein. Furthermore, data processing components of various embodiments in accordance with the present invention are intended to provide exemplary functional relationships and/or couplings between the various elements. It should be noted that many alternative or additional functional relationships or physical connections may be present in a practical system.

It will be appreciated that many applications of the present invention may be formulated. One skilled in the art will appreciate, for example, that a distributed processing architecture may include any system for exchanging data, such as, for example, the Internet, an intranet, an extranet, WAN, LAN, satellite communications, and/or the like. It is noted that a network may be implemented as other types of networks, such as an interactive television (ITV) network as well. The users may interact with the system via any input device such as a keyboard, mouse, kiosk, personal digital assistant, handheld computer (e.g., PalmPilot®), mobile phone and/or the like. Similarly, the invention could be used in conjunction with any type of personal computer, network computer, workstation, minicomputer, mainframe, or the like running any operating system such as any version of Windows, Windows XP, Windows ME, Windows NT, Windows2000, Windows 98, Windows 95, MacOS, OS/2, DOS, BeOS, Linux, UNIX, or any operating system now known or hereafter derived by those skilled in the art. Moreover, the invention may be readily implemented with TCP/IP communications protocols, IPX, Appletalk, IP-6, NetBIOS, OSI or any number of existing or future protocols. Moreover, the system contemplates the use, sale and/or distribution of any goods, services or information having similar functionality described herein.

The computing units may be connected with each other via a data communication network. The network may be a public network and assumed to be insecure and open to eavesdroppers. In one exemplary implementation, the network may be embodied as the Internet. In this context, the computers may or may not be connected to the Internet at all times. Specific information related to data traffic protocols, standards, and application software utilized in connection with the Internet may be obtained, for example, from Dilip Naik, Internet Standards and Protocols (1998); Java2 Complete, various authors, (Sybex 1999); Deborah Ray and Eric Ray, Mastering HTML 4.0 (1997). Loshin, TCP/IP Clearly Explained (1997). A variety of conventional communications media and protocols may be used for data links, such as, for example, a connection to an Internet Service Provider (ISP), over the local loop as is typically used in connection with standard modem communication, cable modem, Dish networks, ISDN, Digital Subscriber Line (DSL), or various wireless communication methods. Data processing systems in accordance with the present invention might also reside within a local area network (LAN) which interfaces to a network via a leased line (T1, T3, etc.). Such communication methods are well known in the art, and are covered in a variety of standard texts. See, for example, Gilbert Held, Understanding Data Communications (1996).

As will be appreciated by one of ordinary skill in the art, various components of the present invention may be embodied as a composition of matter, a method, a system, a device, and/or a computer program product. Accordingly, the present invention may take the form of an entirely software embodiment, an entirely hardware embodiment, or an embodiment combining aspects of both software and hardware. Furthermore, various embodiments of the present invention may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

Data communication may be accomplished through any suitable communication means, such as, for example, a telephone network, intranet, Internet, point of interaction device (personal digital assistant, cellular phone, kiosk, etc.), online communications, off-line communications, wireless communications, and/or the like. One skilled in the art will also appreciate that, for security reasons, any databases, systems, or components of the present invention may consist of any combination of databases or components at a single location or at multiple locations, wherein each database or system includes any of various suitable security features, such as firewalls, access codes, encryption, decryption, compression, decompression, and/or the like.

Where the instant invention embodies a method for performing the various tasks disclosed herein as a software embodiment, computer program instructions may be loaded onto a general purpose computer, special purpose computer, or other programmable data processing apparatus to produce a machine, such that the instructions which execute on the computer or other programmable data processing apparatus create means for implementing the functions specified in the disclosed methods. These computer program instructions may also be stored in a computer-readable memory capable of directing a computer or other programmable data processing apparatus to function in a particular manner, such that the instructions stored in the computer-readable memory produce an article of manufacture including instruction means which implement the functions specified in the disclosed method steps. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the variously disclosed method steps.

Accordingly, the disclosed method steps support combinations of means for performing the specified functions, combinations of steps for performing the specified functions, and program instruction means for performing the specified functions. It will also be understood that each disclosed method step and combinations of method steps may be implemented by either special purpose hardware-based computer systems which perform the specified functions or steps, or suitable combinations of special purpose hardware and computer instructions.

In the foregoing specification, the invention has been described with reference to specific exemplary embodiments; however, it will be appreciated that various modifications and changes may be made without departing from the scope of the present invention as set forth in the claims below. The specification and figures are to be regarded in an illustrative manner, rather than a restrictive one and all such modifications are intended to be included within the scope of the present invention. Accordingly, the scope of the invention should be determined by the claims appended hereto and their legal equivalents rather than by merely the examples described above. For example, the steps recited in any method or process claims may be executed in any order and are not limited to the specific order presented in the claims. Additionally, the components and/or elements recited in any apparatus claims may be assembled or otherwise operationally configured in a variety of permutations to produce substantially the same result as the present invention and are accordingly not limited to the specific configuration recited in the claims.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components of any or all the claims.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted by those skilled in the art to specific environments, manufacturing specifications, design parameters or other operating requirements without departing from the general principles of the same.

We claim:

1. A molecular semaphore device comprising:
    a biomolecular rotary motor comprising an F-ATPase modified via site directed mutagenesis so as to comprise a his-tag on the N-terminus of an F1-α subunit and a cysteine on the F1-γ subunit;
    a fragment of capture probe nucleic acid effectively attached to said biomolecular motor;
    a target nucleic acid fragment adapted for hybridization with said capture probe nucleic acid;
    a signal probe nucleic acid fragment adapted for hybridization with said target nucleic acid; and
    an electromagnetic reporter attached to said signal probe nucleic acid, said molecular semaphore device for use in a rotational assay for the detection of said target nucleic acid fragment.

2. The molecular semaphore device according to claim 1, wherein said probe nucleic acid comprises at least one of DNA and RNA.

3. The molecular semaphore device of claim 1, wherein said capture probe nucleic acid is at least partially single-stranded.

4. The molecular semaphore device of claim 1, wherein said signal probe nucleic acid is adapted to hybridize with said target nucleic acid sequences substantially corresponding to sequences unpaired with said capture probe.

5. The molecular semaphore device of claim 1, wherein said capture probe nucleic acid is suitably adapted for substantially specific recognition of a bio-warfare agent.

6. The molecular semaphore device of claim 1, further comprising at least an array of molecular semaphore devices.

7. The molecular semaphore device of claim 6, wherein said array comprises at least a plurality of capture probe nucleic add fragments suitable adapted for substantially specific recognition of at least a plurality of bio-warfare agents.

8. The molecular semaphore device of claim 1, wherein said capture probe nucleic acid fragment comprises about 15 base pairs.

9. The molecular semaphore device of claim 1, wherein said target nucleic acid fragment comprises about 30 base pairs.

10. The molecular semaphore device of claim 1, wherein said signal probe nucleic acid fragment comprises about 150 base pairs.

11. The molecular semaphore device of claim 1, wherein said electromagnetic reporter comprises at least one of an optical, magnetic and thermal particle.

12. The molecular semaphore device of claim 11, wherein said electromagnetic reporter comprising an optical reporter comprising at least one of a fluorescent bead and an optical scattering particle.

13. The molecular semaphore device of claim 12, wherein said optical scattering particle comprises a colloidal particle from the elemental group of metals.

14. The molecular semaphore device of claim 1, wherein at least one end of said signal probe nucleic acid fragment is biotinylated for attachment with said electromagnetic reporter.

15. The molecular semaphore device of claim 14, wherein said electromagnetic reporter is Streptavidin labeled.

16. The molecular semaphore device of claim 1, wherein said electromagnetic reporter is about 100 nm in diameter.

17. The molecular semaphore device of claim 1, wherein said signal probe is within the persistence length of dsDNA and therefore provides an effectively rigid tether between said biomolecular motor and said reporter.

18. The molecular semaphore device of claim 1, further comprising an electromagnetic readout means comprising at least one of a solid immersion optical flying head, an optical detector, a GMR (Giant Magnetoresistive) sensor, a MRAM (Magnetoresistive Random Access Memory) sensor, a magneto-optical sensor and an electro-optical sensor.

19. A molecular semaphore device suitable for use in a rotational assay, said device comprising:
    a biomolecular rotary motor comprising an F1-ATPase modified via site-directed mutagenesis so as to comprise a his-tag on the N-terminus of an F1-α subunit and a cysteine on the F1-γ subunit;
    a fragment of capture probe nucleic acid effectively attached to said biomolecular motor;
    a target nucleic acid fragment adapted for hybridization with said capture probe nucleic acid;
    a signal probe nucleic acid fragment adapted for hybridization with said target nucleic acid;
    an electromagnetic reporter attached to said signal probe nucleic acid; and
    an optical device, comprising at least one of an optical microscope and a near-field excitation source with dimension effectively below the wavelength of excitation, for detecting the target nucleic acid fragment.

20. The molecular semaphore device of claim 19, where said near-field excitation source comprises at least one of a near-field aperture, a tapered optical fiber, a solid immersion lens and a surface plasmon source.

* * * * *